(12) United States Patent
Virkamäki et al.

(10) Patent No.: US 8,781,752 B2
(45) Date of Patent: Jul. 15, 2014

(54) MEASURING CONTROL METHOD AND ARRANGEMENT

(75) Inventors: Antti Virkamäki, Vantaa (FI); Kristian Ranta, Helsinki (FI); Jukka Planman, Helsinki (FI); Tuomas Planman, Espoo (FI); Henri Andell, Espoo (FI)

(73) Assignee: Mendor Oy, Espoo (FI)

( * ) Notice: Subject to any disclaimer, the term of this patent is extended or adjusted under 35 U.S.C. 154(b) by 0 days.

(21) Appl. No.: 13/384,227

(22) PCT Filed: Jul. 14, 2010

(86) PCT No.: PCT/FI2010/050595
§ 371 (c)(1),
(2), (4) Date: Mar. 23, 2012

(87) PCT Pub. No.: WO2011/007051
PCT Pub. Date: Jan. 20, 2011

(65) Prior Publication Data
US 2012/0173161 A1    Jul. 5, 2012

(30) Foreign Application Priority Data
Jul. 15, 2009  (FI) ..................... 20095791

(51) Int. Cl.
*G01N 33/48*      (2006.01)

(52) U.S. Cl.
USPC .......................................... 702/19

(58) Field of Classification Search
USPC .......................................... 702/19
See application file for complete search history.

(56) References Cited

U.S. PATENT DOCUMENTS

| | | |
|---|---|---|
| 8,317,699 B2 * | 11/2012 | Weinert et al. ............. 600/365 |
| 2005/0272640 A1 | 12/2005 | Doyle, III et al. |
| 2008/0119705 A1 | 5/2008 | Patel et al. |
| 2008/0234943 A1 | 9/2008 | Ray et al. |
| 2009/0018406 A1 | 1/2009 | Yodfat et al. |

FOREIGN PATENT DOCUMENTS

WO     2007093482     8/2007

* cited by examiner

*Primary Examiner* — Jerry Lin
(74) *Attorney, Agent, or Firm* — Fasth Law Offices; Rolf Fasth

(57) ABSTRACT

The method is for controlling a measurement process of blood glucose of a patient. At least one repeatedly occurring even is selected within a period of time. A blood glucose measurement difference data is obtained that is associable to the event. Trend data is calculated from the difference data. The measurement process is controlled by using the trend data. Also an arrangement, computer program product and a device are disclosed.

13 Claims, 7 Drawing Sheets

| | Descr. | Time | Breakfast | change | Time | Lunch | change | Time | Dinner | change | Time | Bedtime | change to next m |
|---|---|---|---|---|---|---|---|---|---|---|---|---|---|
| Block 1 | | | | | | | | | | | | | |
| Day 1 | Meas. #1 | 9:02 | 5,6 | 4,6 | 13:00 | 8,4 | 4,7 | 17:48 | 7,5 | 4,8 | 23:32 | 13,2 | -6,5 |
| | Meas. #2 | 11:00 | 10,2 | | 15:01 | 13,1 | | 19:33 | 12,3 | | | | |
| Day 2 | Meas. #1 | 8:33 | 6,7 | 2,9 | 12:44 | 9,1 | 2 | 18:05 | 8,3 | 5,9 | 23:45 | 14,6 | -9,5 |
| | Meas. #2 | 10:37 | 9,6 | | 14:30 | 11,1 | | 20:40 | 14,2 | | | | |
| Day 3 | Meas. #1 | 8:55 | 5,1 | 7,1 | 13:22 | 8,3 | 1 | 17:34 | 6,5 | 2 | 23:55 | 9,2 | |
| | Meas. #2 | 10:40 | 12,2 | | 15:55 | 9,3 | | 19:40 | 8,5 | | | | |
| Block 2 | | | | | | | | | | | | | |
| Day 4 | Meas. #1 | 9:00 | 6,7 | 1,7 | 13:02 | 8,1 | 3,1 | 18:30 | 7,3 | 2,8 | 23:12 | 10,3 | -4,2 |
| | Meas. #2 | 10:38 | 8,4 | | 15:15 | 11,2 | | 20:15 | 10,1 | | | | |
| Day 5 | Meas. #1 | 8:50 | 6,1 | 1,7 | 13:10 | 6,5 | 2,2 | 18:03 | 7,6 | 1,6 | 22:56 | 9,1 | -2,3 |
| | Meas. #2 | 10:12 | 7,8 | | 15:40 | 8,7 | | 20:22 | 9,2 | | | | |
| Day 6 | Meas. #1 | 8:35 | 6,8 | 0,3 | 12:33 | 7,4 | 2,2 | 17:40 | 7,4 | 0,8 | 0:12 | 12,2 | |
| | Meas. #2 | 10:30 | 7,1 | | 14:48 | 9,6 | | 19:33 | 8,2 | | | | |
| Block 1 | Meas#1 | | 5,8 | 4,9 | | 8,6 | 2,6 | | 7,4 | 4,2 | | 12,3 | -8,0 |
| | Meas#2 | | 10,7 | | | 11,2 | | | 11,7 | | | | |
| Block 2 | Meas#1 | | 6,5 | 1,2 | | 7,3 | 2,5 | | 7,4 | 1,7 | | 11,9 | -3,3 |
| | Meas#2 | | 7,8 | | | 9,8 | | | 9,2 | | | | |
| Interpretation | | | Good | <2 | | interm. >2<4 staying the same | no change | | Good | <2 | | interm. >-4 | |
| | | | Getting better | 1,2<4,9 | | | | | Getting better | 1,7<4,2 | | getting better | |

Fig 6

MEASURING CONTROL METHOD AND ARRANGEMENT

PRIOR APPLICATIONS

This is a U.S. national phase patent application that claims priority from PCT/FI2010/050595 filed 14 Jul. 2010, that claims priority from Finnish Patent Application No. 20095791, filed 15 Jul. 2009.

TECHNICAL FIELD OF INVENTION

The invention relates to a measuring method and arrangement for measuring and analyzing e.g. blood glucose levels of a patient and for controlling the measurement process.

BACKGROUND OF THE INVENTION

Blood glucose measurement of a diabetes patient is a frequently occurring task. Each measurement requires both manual work and suitably also some computerized analysis work.

Blood glucose monitoring and adjustment of the treatment regimen is important in the management of diabetes. This requires measurement of glucose values (typically with a portable monitor, from a blood sample), recording the results and later analyzing the results. The results can be used to better the treatment regimen and balance. Typically, wireless or wired data transfer methods can be used to transport results from the meter to a local or server-based database for the analysis.

Finding the optimal balance between food intake, insulin dosage, exercise and other factors affecting the blood glucose level is a difficult task, especially to a person who has just been diagnosed with diabetes and who needs to change his/her habits, and most importantly, who needs to learn a way to monitor the blood glucose level in an efficient way. One method of learning is to divide the problem into multiple components, guide person's attention to a small number of issues (e.g. one) at a time and to solve thus the issues one-by-one.

The measurement processes of the prior art require an unnecessarily large number of measurements yet providing measurement data of insufficient quality and understandability especially for a new diabetes patient. The measurement processes of the art also lack adaptability according to the current needs of the patient and/or medical personnel.

Typical solutions include graphs and tables of values. The graphs and average values, however, are not suitable to make decisions on the improvement of measurement process or a treatment related to the measurement process. The results of these existing software typically require a trained user and further analysis of the results, which is time consuming.

Patent application WO2007093482 describes a device and method for managing data relating to blood glucose level for a person. In the method, blood glucose level is measured before and after an event to obtain data pairs, and the data pairs are processed, and based on the processed data pairs, graphics and/or text is displayed on a display means. The publication fails to teach a method where the measurement data is utilized for controlling the measurement process. Further, the solution described displays the results on a 2D-table in a manner that makes it difficult to make any concrete adjustments to the treatment. The table may be difficult to understand, requiring further analysis. Further, the publication fails to teach a method to analyze the treatment balance and its development over different periods of time. Furthermore, the publication fails to teach a method to target the measurements, and interpret the results in a form providing instant basis for assessing and improving the treatment balance.

Patent application US20080234943 discloses a diabetes management information providing program for use in a diabetes management system. The program has an object module, where messages have patterns from patient data indicative of variability by time of day, day in week or time intervals Patent application WO2008071218 discloses a monitoring device, e.g a personal battery-powered diagnostic handheld device. The device relates to stored measurement values of an analyte test element port to a medical useful compliance range.

Patent application WO2005093629 discloses a display device for diabetic patients. The device displays a graph showing time relative to habitual meals and blood glucose level, in which glucose level at point of time of meal, mean or median value of pre and post meal glucose values are indicated.

Patent application US20080119705 discloses a diabetes managing system for managing diabetes using a medical device and a consumer electronic device.

The system has a connector that is removably coupled to a consumer electronic device to facilitate communication between the medical device and the consumer electronic device.

Patent application US20000177147 discloses an insulin therapy managing apparatus for treating diabetic persons. The apparatus has an insulin timing module initiating delivery of insulin in time relation to when a meal is to be consumed by user, and adjusting the delivery of insulin based on this information.

Patent application US20050272040 discloses a computer-implemented control method for insulin dosing for diabetics. The method involves estimating preprandial dosage of insulin based on observed postprandial glucose response to meal, insulin sensitivity and preprandial insulin dose of current day.

A method and arrangement that gradually guides the patient towards an efficient blood glucose measurement and controlling process by improving gradually the quality and usefulness of data obtainable from the measurements is desired. Such method advantageously guides patient's attention at each point of time to a small number of issues that require improvement. Eventually, after the issues are under control, the number of measurements needed and amount of guidance provided to the patient should be minimized.

OBJECT OF THE INVENTION

An object of the present invention is to provide at least one of a method, an arrangement, a computer program product and a device for controlling the blood glucose measurement process. The method may include recording, analyzing and/or assessing the measurement results of a diabetes patient. Another object of the invention may be to provide means that help patient focus on measuring events that need attention. Yet another object of the invention may be to gradually reduce the number of activities and thus, usage of e.g. computing resources, needed to monitor and control blood glucose level of a patient. Still yet another object of the invention may be to provide technical means for improving the quality of diabetes treatment.

SUMMARY OF THE INVENTION

An aspect of the invention is a method for controlling the measurement process of blood glucose of a patient. The method is characterized in that it comprises any, any combination or all of the steps of selecting, specifying or recognizing at least one event from a repeatedly occurring period of time, obtaining blood glucose measurement difference data that is associable to the event, calculating trend data from the difference data, and controlling the measurement process using the trend data.

The period of time may be e.g. a day or any other repeatedly occurring period of time.

The repeatedly occurring event may represent e.g. a specific habitual meal, e.g. lunch, or exercise or other event that may have a significant impact to the blood glucose level of a patient.

The blood glucose measurement difference data may be obtained using e.g. at least two measurements for each occurrence of the event in a plurality of periods of time.

The trend data may comprise e.g. at least one difference data value and the direction of change of the difference data over time.

The difference data value may be e.g. a single value or a combined value, e.g. an average of a plurality of difference data values. A single difference data value may be obtained e.g. by subtracting a first measurement value of an event from a second measurement value of a measurement pair of the same event or vice versa.

Suitably, the method is executed or is at least executable using an arrangement comprising at least one computer comprising a processor, memory and data communication means. The computer may be e.g. a server computer or a terminal device.

The measurements related to the events may be assigned to the events in various different ways. These include manual tagging, setting up time windows, or a combination of these, or other suitable selection and/or recognition methods.

An event may be associated with a time window which suitably has a pre-determined length. For example, first measurement related to an event starts the time window of approximately two hours, at the end of which the second measurement should take place.

The measurement data may comprise e.g. any or any combination of the following: timing of a single measurement, blood glucose level of a single measurement and variance or difference between the measurement values of the at least two measurements within a time window relating to an event. The trend data may indicate, e.g. the average blood glucose level difference and direction of change of the average difference data of the blood glucose level over time.

Corresponding events are recognized events, that are related to a similar event, e.g. a habitual meal, e.g. a breakfast, lunch or dinner. For example, a corresponding event may be the event of the same meal time but from different days.

Suitably, the method is executed or executable using a computer arrangement. The computer arrangement may comprise a server computer and/or a terminal device, e.g. mobile device, e.g. a cellular phone or a blood glucose meter that is communicatively connectable to the server computer.

The at least two, preferably two, glucose measurements are also referred hereinafter as a "pair measurement". Suitably, the pair measurement comprises a pair of measurements that occur within time windows set up before and after the event, or before and after the event as identified by manual tagging, or a combination of these.

The blood glucose meter may comprise a timer which reminds the patient about the second measurement after e.g. 2 hours has passed from the first measurement of a pair measurement. The timer function may be activated automatically e.g. when a patient measures his/her blood glucose level using the blood glucose meter and there is no timer function active. The timer function may also be accomplished using separate components or devices such as mobile phones.

An event, e.g. a meal, may be linked to the time windows. Alternatively or additionally, at least one measurement of the pair measurements may be recognized/tagged manually, for example with user interface buttons of a measuring device, i.e. a blood glucose meter. The second pair measurement can be thereafter recognized based on its timestamp (e.g. 2 hours +/−15 minutes from the first measurement), or also tagged manually. Furthermore, measurements may be recognized as pair measurements by their timestamp.

The timing information may include e.g. the number and percentage of measurement values that fit in the recognized time windows.

Suitably, the measurement process is usable for improving the treatment regimen of a diabetes patient.

The step of controlling the measurement process may have e.g. the goal of improving the relevance of the obtained measurement data. Another goal may be e.g. helping the patient to achieve measurement results that contribute to the treatment of a disease, e.g. diabetes. For example, the controlling step may comprise sending a reminder about timely measurement of blood glucose or sending a reminder about paying attention to food intake (e.g. proportion or carbohydrates) during a meal. In an embodiment, the controlling step may comprise determining, whether a certain measurement is necessarily required or not.

In an embodiment, the blood glucose measurement data may comprise also information about the change of blood glucose level between pre- and post-measurements related to a specific event, within a time window and/or across time windows.

In an embodiment, the trend data may comprise trend information about the change of blood glucose level data.

In an embodiment, the absolute blood glucose level information and/or its trend data is used for the control of the measurement process if e.g. the average difference data within a time window is within pre-determined limits.

In an embodiment, the absolute blood glucose level is calculated to be an average from the first or second measurements of a plurality of specific events, e.g. lunch.

The average difference data between the measurements of a plurality of corresponding events, e.g. a lunch event in different days, may be calculated e.g. by subtracting the average of second measurement values from the average of the first measurement values of the events or vice versa.

In an embodiment, the trend data of the invention comprises monitoring the value of the pair measurement, and its change over time in pair measurements of corresponding events. Suitably, the trend data comprises information about the state of the pair measurement, and direction of change. For example, the measured values may be "bad" and "getting better" or "fair" and "getting worse" over time. This may be particularly useful for identifying needs for improvements of the regimen, and monitoring the effects of such changes. For example, the system may identify, using the trend information, a time window where measurement values are "bad" and "unchanging" and notify the patient that this event (e.g. meal) requires more attention and thus e,g. the timely measurements are especially important for this event. After changing the regimen the system may monitor if the balance is improving in the intended way, e.g. if the measured values related to the event have now a "fair" and "getting better" trend.

In an embodiment, the step of controlling the measurement process comprises displaying needs for changes to a treatment regimen, and monitoring the effect of such changes. The step of controlling the measurement process may be at least partially accomplished using the processing power, data storage and data input/output means of a blood glucose monitor. At least some steps of the method may also be performed using data storage and processing power of a remote server and/or other mobile devices.

In an embodiment, the pair measurement data may comprise the difference between the measurement values. The trend data may advantageously be calculated from this "difference only" data. The actual blood glucose levels may be ignored at this phase, provided that no risk of hypoglycemia exists. The information about average blood glucose levels may be included in the control process once the variance within time windows is sufficiently under control.

The controlling of the measurement process may comprise altering the guidance status related to the event. The guidance status of the event may correspond to the degree of attention required from the patient and/or medical personnel. The guidance status may for example control the presentation, nature, timing and/or frequency of messages sent to the patient. The guidance status may be e.g. "does not need guidance", "needs some guidance", "needs extensive guidance" or "needs consultation from medical staff". The guidance status may also comprise information about what kind of guidance is needed. For example, user's attention may be drawn to the need of a measurement (e.g. when the patient has not provided measurement data when such data were needed by the treatment process), to the timing of the measurement, to the monitoring of the difference between the values of the pair measurement or to the monitoring the average level of blood glucose across a plurality of measurements.

The pair measurements related to events may represent e.g. the typical meal times of a day, e.g. breakfast, lunch, dinner and evening snack. The corresponding pair measurements are the pair measurements of the same meal time but from different days.

The targeting of measurements enables the effective gathering of pair measurement values in a diabetes treatment process. In the first phase of an exemplary process, the patient is taught to perform the measurements in a sufficiently regular manner, e.g. right before a meal and two hours after the meal. If the measurements are not provided regularly enough, the system increases the amount of control (e.g. increases the number of reminders or changes the nature of reminders sent to the patient) of the measurement process.

After a sufficient number of measurement values having sufficiently accurate timing have been gathered, the method may draw patient's attention to issues that patient needs to concentrate on. For example, the method may send or display a notice that the after-meal measurement value related to a meal event is significantly higher than the pre-meal value, implying a suboptimal treatment balance. Furthermore, if the after-meal measurement value has lately been getting even higher compared to the pre-meal measurement, the system can also indicate that the trend is getting worse. The patient may now change his/her treatment regimen to result in a more stable glucose levels (less variance) related to an event. In an embodiment, the method may also request additional measurements related to an event.

After the balance related to all established events in the system is sufficiently stable, the method may proceed to advice the user to move to the next phase of the treatment process—e.g. lowering the average glucose level closer to an individually set target level.

When at least the timing and variance and possibly also the average level of blood glucose are under control, the method may allow the patient to reduce the number of measurements needed. The reduced number of measurements reduces the amount of resources, e.g. lancets and measurement strips, needed to monitor the blood glucose level. The reduced amount of guidance also makes the system more convenient to use as guidance is not provided about events that are already well under control.

The healthy region of blood glucose levels is quite narrow. If there is a large variability in the glucose levels, it may be difficult to reach the healthy levels. An embodiment of the invention may make it possible to effectively guide the measuring process to first reduce the variation of results related to events, and, once the variation is confined into a sufficiently narrow range, eventually guide the patient to lowering the long-term glucose levels to the healthy region.

The controlling of the measurement process may send a message to a mobile device which may be e.g. a cellular phone or a blood glucose monitor (i.e. blood glucose metering device) or any other suitable mobile or non-mobile device communicatively connectable to a data communication network.

In one embodiment of the invention, some or all of the functionalities, including analysis and reminders, may be included in the portable blood glucose monitor. In an embodiment the functionalities may be divided between the monitor, data server, mobile phone, personal computer and other devices and systems in ways that are apparent to those skilled in the art.

The controlling of the measurement process may also comprise displaying said trend data (analysis data) and/or guidance status on a user interface of a web application.

Another aspect of the invention is an arrangement for controlling the measurement process of blood glucose of a patient. The arrangement may comprise at least one server computer. The arrangement is characterized in that it comprises means for selecting, specifying or recognizing at least one event from a repeatedly occurring period of time, obtaining blood glucose measurement difference data that is associable to the event, calculating trend data from the difference data, and controlling the measurement process using the trend data.

Yet another aspect of the invention is a computer readable media comprising a software program product for controlling the measurement process of blood glucose of a patient. This aspect is characterized in that the software program product comprises computer executable program code for controlling the measurement process of blood glucose of a patient. The program product is characterized in that it comprises instructions for selecting, specifying or recognizing at least one event from a repeatedly occurring period of time, obtaining blood glucose measurement difference data that is associable to the event, calculating trend data from the difference data, and controlling the measurement process using the trend data.

Still yet another aspect of the present invention is a blood glucose meter communicatively connectable to the arrangement of an embodiment of the present invention. The blood glucose meter may be adapted to send measurement data to e.g. the server computer of the arrangement and/or to receive measurement control data from the server computer of the arrangement.

Some embodiments of the invention are described herein, and further applications and adaptations of the invention will be apparent to those of ordinary skill in the art.

BRIEF DESCRIPTION OF DRAWINGS

In the following, the invention is described in greater detail with reference to the accompanying drawings in which FIG. 6 shows exemplary input and trend data of the method of an embodiment of the present invention.

DETAILED DESCRIPTION OF THE DRAWINGS

Figure 1:
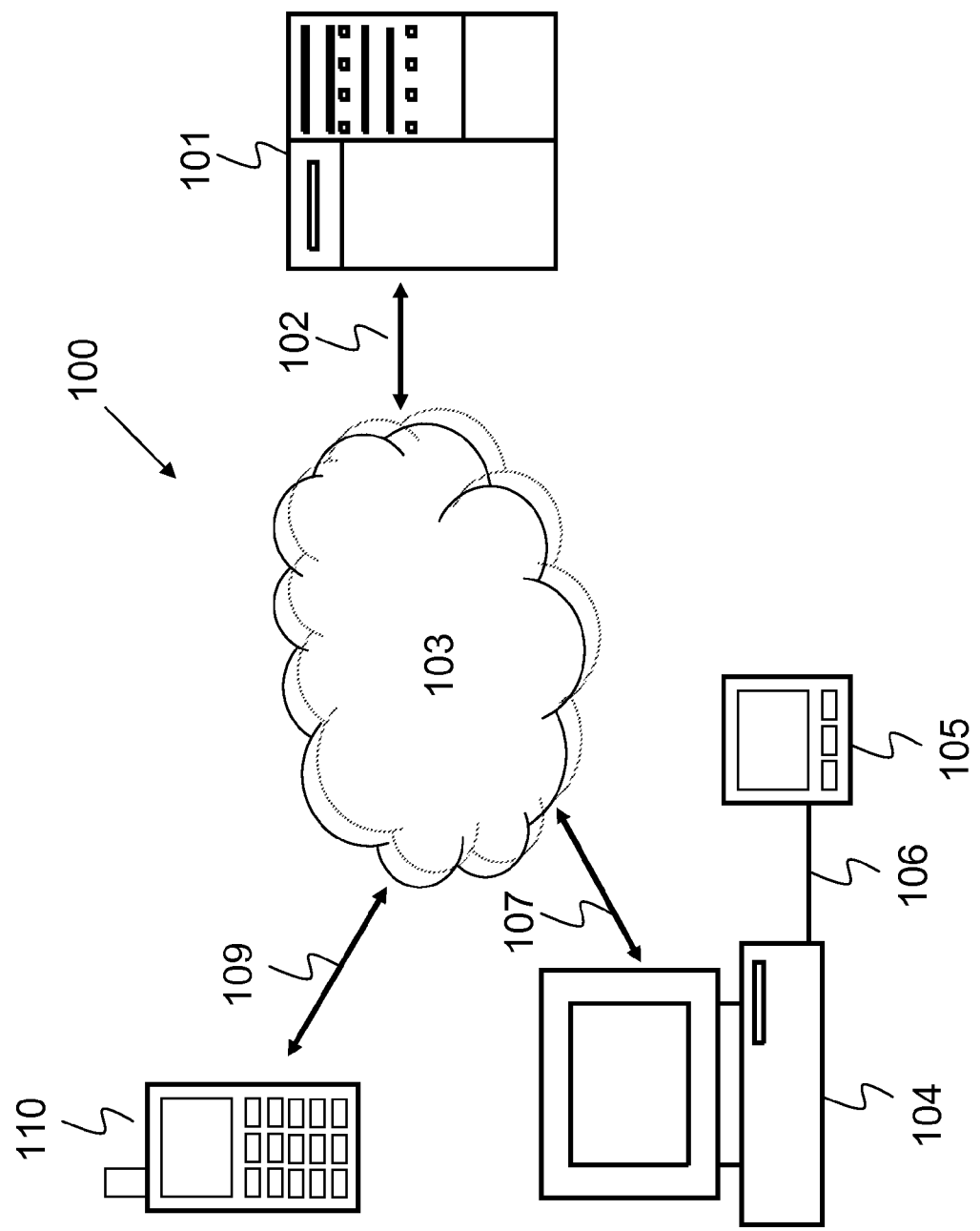
FIG. 1 shows an exemplary arrangement according to an embodiment of the present invention.

FIG. 1 shows an exemplary embodiment of an arrangement according to an embodiment of the present invention. The arrangement 100 comprises a server, e.g. a web server 101 that is communicatively coupled 102 to a data communication network 103, that comprises e.g. Internet. The shown arrangement also comprises a terminal device 104, e.g. a PC computer that is also communicatively coupled 107 to the data communication network 103. A measuring device, e.g. a blood glucose meter 105 is communicatively coupled 106, e.g. via USB cable, to the terminal device 104 to facilitate e.g. measurement data transfer between the measuring device 105 and the terminal 104. In an embodiment (not shown in FIG. 1), the blood glucose meter may be directly connected to the data communication network 103 e.g. via GSM, 3G, WLAN or other suitable data communication means. This way, the blood glucose meter 105 may essentially comprise the needed functionality of both the blood glucose meter and the terminal 104. The terminal suitably runs a browser or other software having a user interface that communicates with a web application running on the server 101. The web application is arranged to collect measurement data from the measuring devices 105 and analyze the collected data. The arrangement may also comprise e.g. a mobile communication device, e.g. a cell phone 110 that is communicatively coupled 109 to a suitable data communication network, e.g. GSM/GPRS, 3G and/or a WLAN network. The cell phone may also be used for sending data to the server e.g. via SMS or a web browser and/or for receiving data, e.g. measurement instructions, from the server 101. In an embodiment, the cell phone 110 may comprise the measuring device 105.

Figure 2:
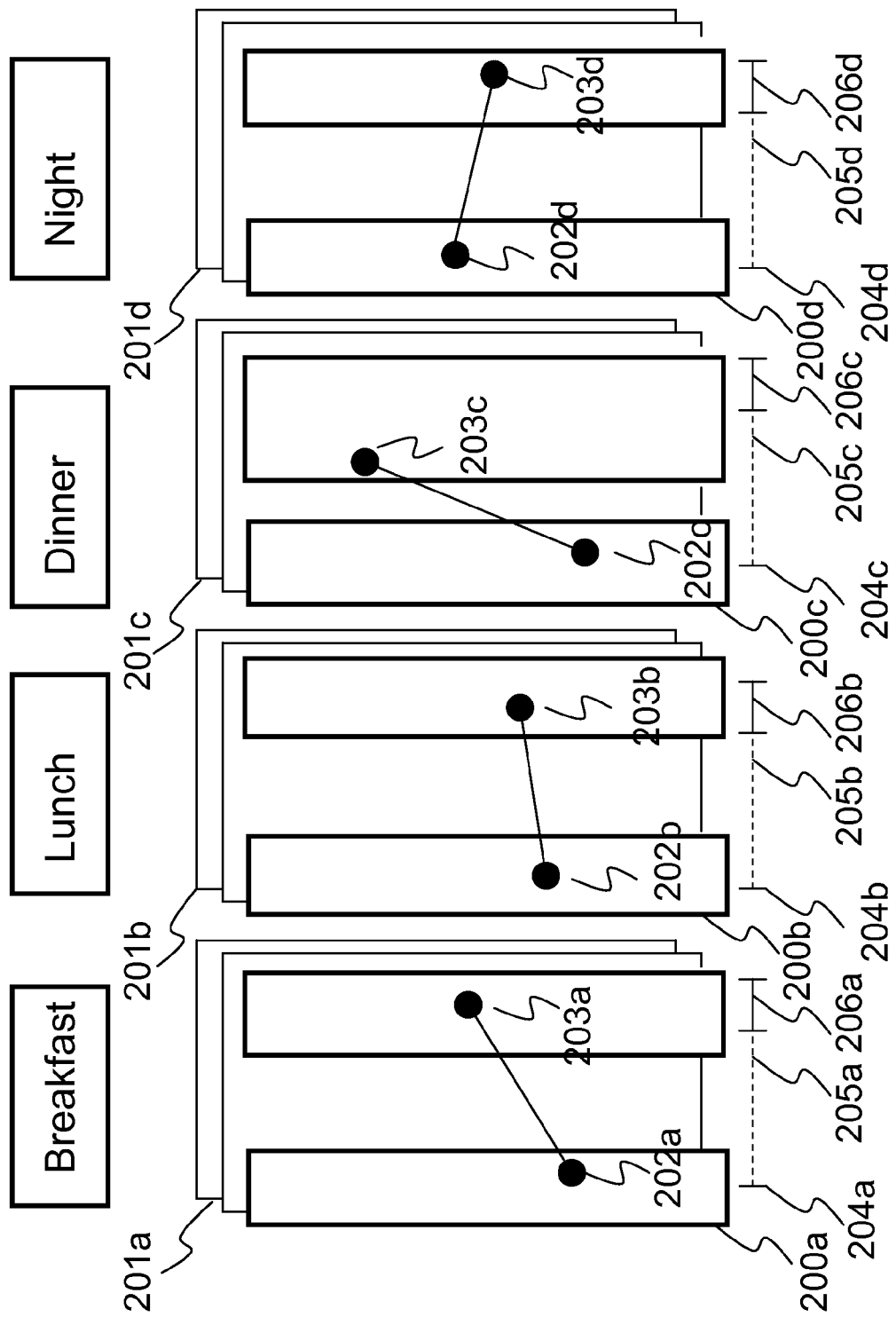
FIG. 2 shows measurement modules and measurement values according to an embodiment of the present invention.

FIG. 2 depicts an exemplary measuring method according to an embodiment of the present invention. Within a re-occurring period of time, suitably a day, events (such as meals) are recognized. Measurements are linked to the events 200a-d, as pair measurements: pre-measurements 202a-d and post-measurements 203a-d, related to the respective events 200a-d. The measurements may be linked to the event by pre-determined or adaptive time windows, or manual tagging, where an event is identified and the measurement is assigned to the event manually by the user. In an exemplary embodiment, each of the events represent a meal time (e.g. breakfast, lunch, dinner, evening snack) within a day. Related to each event, a plurality, suitably a pair of measurements 202a-d, 203a-d, takes place. Optimally, but not necessarily, the later of the measurements, i.e. 203a-d, occurs after a fixed period of time after the earlier measurement 202a-d. Such fixed period of time may be e.g two hours plus/minus 15 minutes. In the figure, reference numerals 204a-d represent the occurrence of the first measurement of a module. A module typically represents e.g. an event that may occur repeatedly, e.g. daily. The reference numerals 206a-d represent the optimal time frame for the second measurement. The reference numerals 205a-d represent the optimal time between the first and the second measurement. Measurement data of each module is stored in the system from a plurality of days. The event measurements of the previous days are represented by reference numerals 201a-d in the figure.

Figure 3:
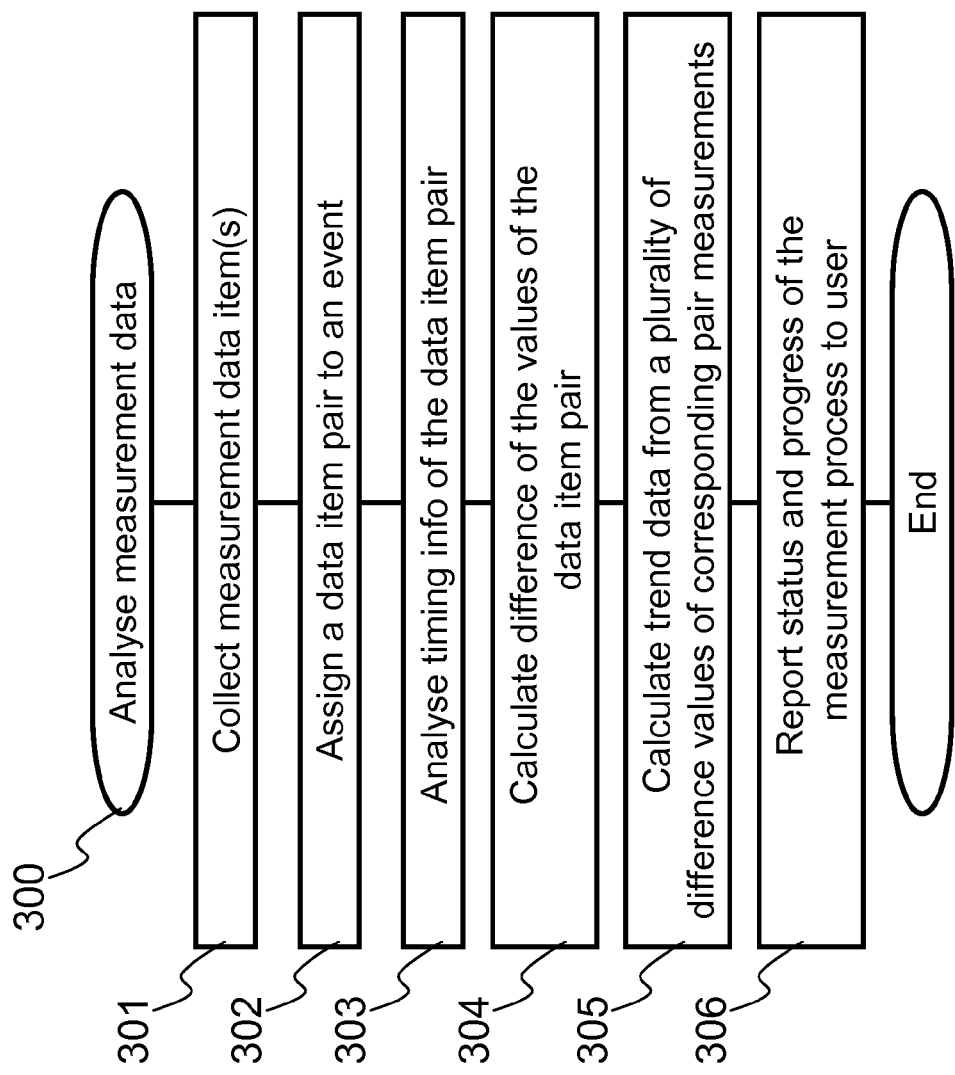
FIG. 3 shows a flow chart about an exemplary method of analyzing measurement data according to an embodiment of the present invention.

FIG. 3 depicts an exemplary embodiment of analyzing 300 the collected measurement data of a module (200a-d in FIG. 2) and calculating trend data from the earlier corresponding modules (201a-d in FIG. 2). First, measurement data items, suitably a pair of data items (e.g. 202a and 203a in FIG. 2), are collected 301. Based on the time of measurement, the data items are assigned 302 to a suitable module (e.g. 200a in FIG. 2). To obtain information about the reliability and quality of the measurement data, the time of measurement of the data items is analyzed 303. Data that is obtained from a measurement at a non-optimal time is less reliable and valuable than data that is obtained from a measurement occurred at optimal time. For example, in an embodiment, the optimal times for blood glucose measurements are right before a meal and about two hours after the meal. Data items that have been measured at non-optimal time may be e.g. discarded from the later analysis and the patient may be informed about insufficient quality of measurement data. In an embodiment, measurement data of insufficient quality e.g. because of bad timing, may trigger a guidance mechanism for the module. Such guidance mechanism may e.g. remind the patient about timely measurement of blood glucose using e.g. SMS messages delivered to a mobile phone or to a blood glucose monitor. In step 304, difference of the values of the (pair of) measurement data items is calculated. In other words, it is observed, how much higher/lower the later measurement value (e.g. 203a in FIG. 2) is in comparison to the earlier measurement value (e.g. 202a in FIG. 2) of the module. In optimal situation, the difference between the measurement values is e.g. zero. The calculated difference value is then compared to earlier difference values of the same module, e.g. from earlier days, and a trend is calculated 305. The trend informs, whether the difference values are moving towards the optimum value ("getting better") or whether they are moving away from the optimum value ("getting worse"). The difference data ("status") and trend data ("progress") may then be reported 306 to the user, e.g. a diabetes patient. The reporting may occur with the data output interface of the blood glucose meter or other means e.g. through a web application or as an SMS to a cellular phone or any other suitable means of communication. If the difference data is around the optimal value, then the analysis may, instead of (or in addition to) monitoring the difference in pair measurements, concentrate on monitoring the absolute (average) blood glucose level of the patient and its development trend. This way, the process guides the patient first to manage the variance in blood glucose levels related to events and then, once variance is under control, guides the patient to manage the average blood glucose level.

Figure 4:
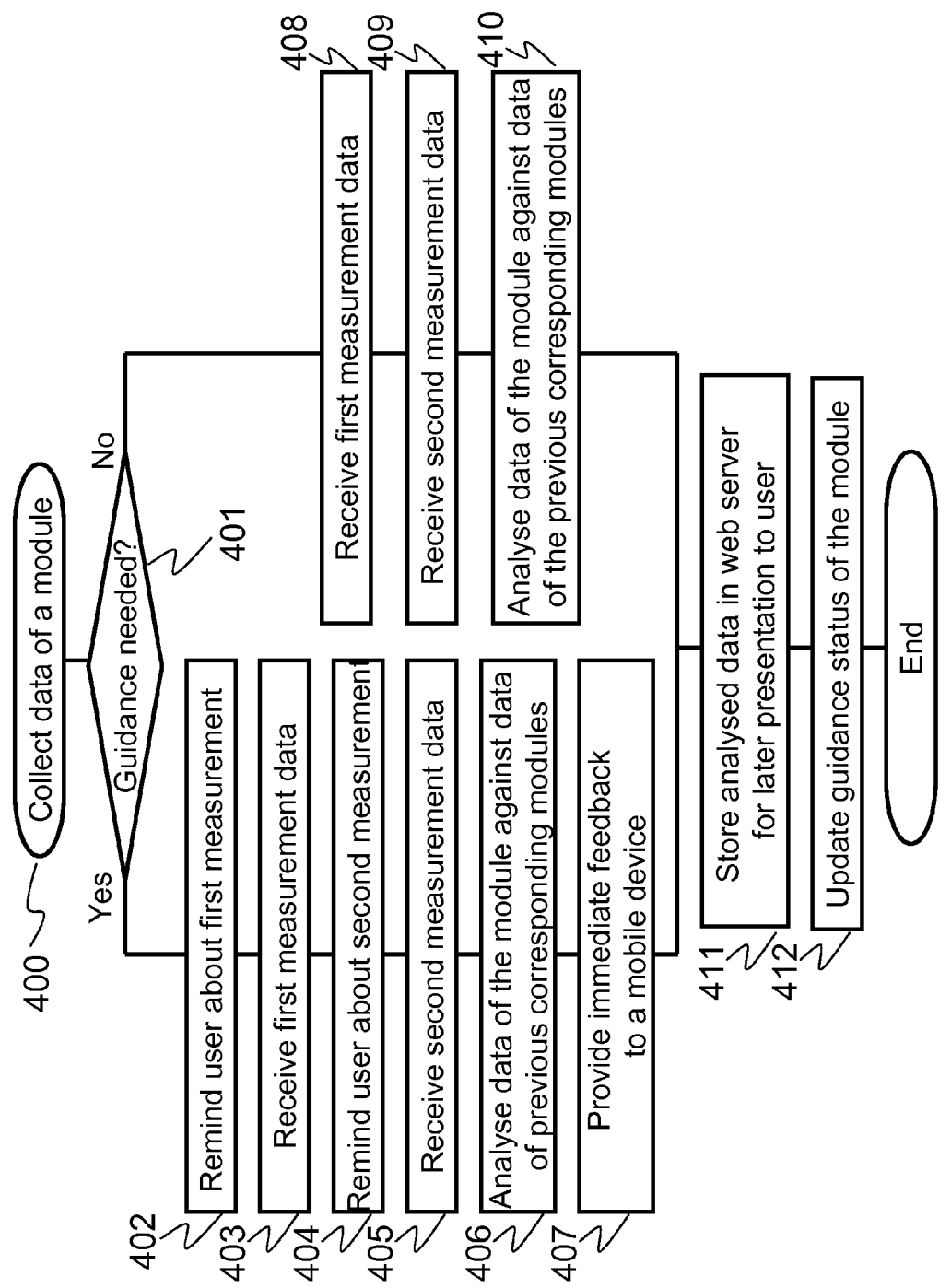
FIG. 4 shows a flow chart about an exemplary method of executing the measurement process according to an embodiment of the present invention.

FIG. 4 depicts an exemplary process of collecting measurement data 400 of a module (e.g. 200a in FIG. 2). For each module, information may be maintained to indicate whether the patient needs guidance in the measurement process for this module. The guidance may be e.g. sending of reminders or instructions to the patient e.g. via SMS or highlighting the issues needing attention in the user interface of a web application. The need for such guidance is checked in step 401. Guidance may be needed, for example, if the timing of the measurements is not optimal, the measured blood glucose variance within the time window is too big or if the trend (direction of change over time) of the difference values is "getting worse".

If, according to the data of the system, guidance is needed, then a guided data collection process starts with step 402 where the patient is reminded about the first measurement of the module, e.g. via a SMS or other message. Then the first measurement data item is received 403. When a suitable amount of time (e.g. approximately two hours) has passed from the first measurement, the user is reminded about the second measurement 404 e.g. via a SMS message. Once the second measurement data item is received 405, the data is analyzed 406 utilizing e.g. a method depicted in FIG. 3 and immediate feedback is provided to the mobile device of the patient e.g. via an SMS message.

If no guidance is needed in step 401, then the system does not remind the patient about the measurements and receives the first measurement data item 408 and second measurement data item 409 and analyses the data 410 using e.g. the method taught in the flow diagram of FIG. 3.

After the data has been collected and analyzed, the collected and analyzed data is stored 411 e.g. in the database of the web server (101 in FIG. 1) for later use, e.g. for presentation to the user through a web application. Finally, the guidance status of the module may be updated 412 according to the measurement and/or trend data e.g. from "guidance needed" to "guidance not needed" or vice versa.

Figure 5:
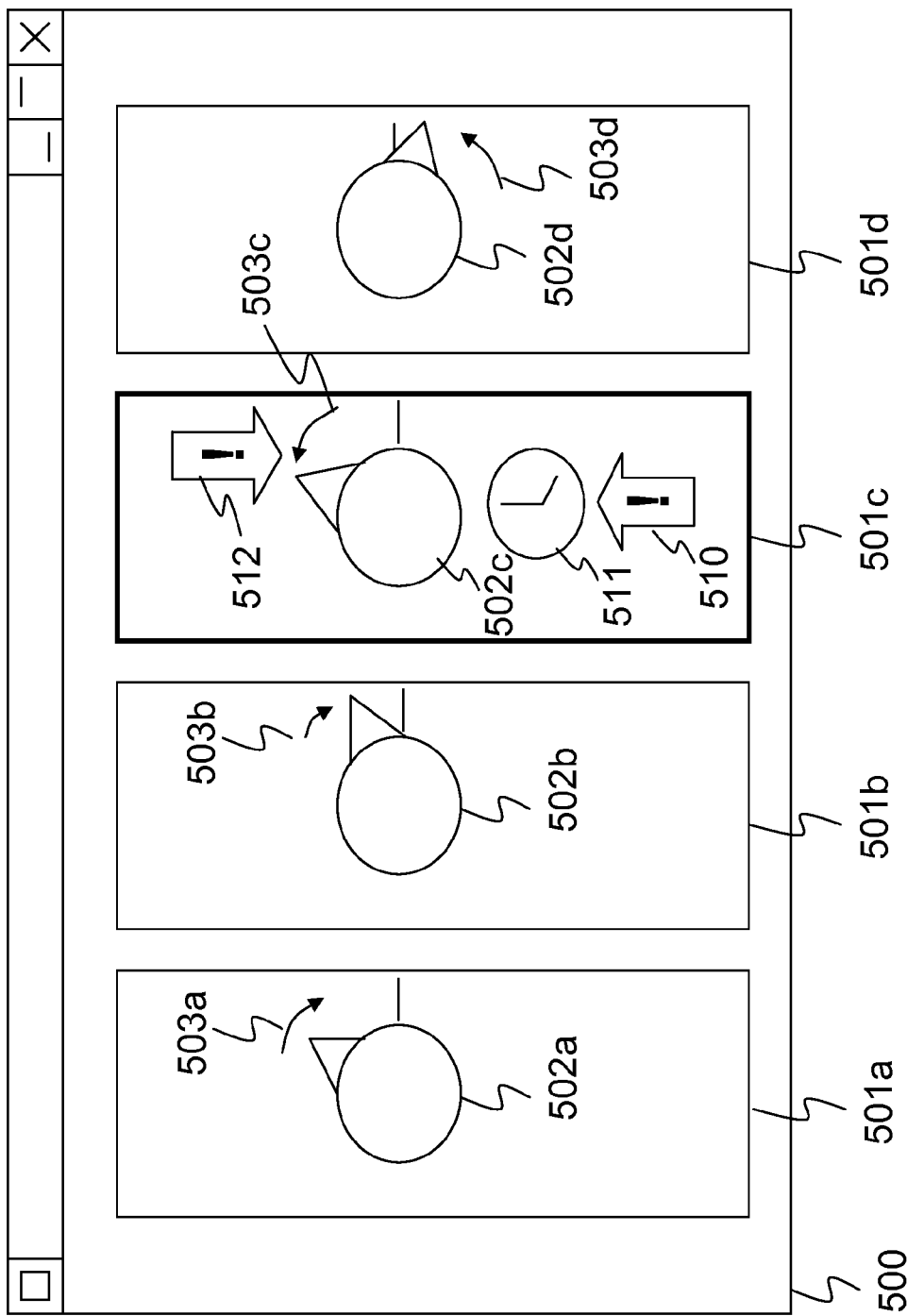
FIG. 5 shows an exemplary user interface usable for viewing the analysis and measurement process control data according to an embodiment of the present invention.

FIG. 5 shows an exemplary user interface 500 of a web application according to an embodiment of the present invention. Each of the measurement modules (200a-d in FIG. 2) of a day is depicted in a separate "box" 501a-d. For each module, the measured difference is illustrated by the symbol 502a-d. The trend (i.e. "getting better" or "getting worse") is illustrated by the arrow 503a-d. In the shown figure, module 501c contains issues that need attention. Therefore, the module is highlighted and user's attention is drawn 510 to measurement times 511 and to the "getting worse" trend 512 which is accompanied by the relatively high difference value described by the upwards pointing arrow. In an embodiment, the patient is notified about the issues needing attention also by e.g. a SMS delivered to his/her mobile phone. The patient may now take some corrective action, e.g. perform the measurement in a more timely manner and/or adjust his/her diet, insulin dosage or exercise amount to correct the high difference value and trend value.

FIG. 6 depicts an exemplary set of measurement and trend data usable in an embodiment of the present invention. The data is shown in a table 600 which contains time windows 601a-d as columns of the table and measurement data 602a-b, trend data 603 and interpretation data 604 of the time windows as rows of the table. The measurement data has been organized into two blocks of three days each. There may be a change in the treatment between the blocks. For each time window ("breakfast", "lunch", "dinner" and "bedtime") and day, the time of measurement and the measurement value of the pair measurement are recorded. Then, the change between first and second measurement is calculated. Note that for the "bedtime" time window, the first measurement of the "breakfast" time window acts as the second measurement.

To analyze the measurement data, the change of blood glucose value is calculated for each event (in the column "change"). The average change within the blocks may also be calculated from these values.

To analyze the measurement data, averages of the change between first and second measurements within a block (of three days) are calculated for each time window. Because the average change level of the most recent measurements is 1.2, i.e. below 2, the current blood glucose change level (difference data) is deemed to be "good".

In order to be able to control the measurement process, also the trend (direction of change) of the difference data needs to be calculated. In this simplified example, the trend is obtained from the difference values of the average measurements. For example, in the "breakfast" time window, the average difference in the first three-day block of measurements is 4.9 whereas the average difference in the second block is 1.2. There thus is a "getting better" trend because the difference is moving towards the optimum, i.e. zero. Now the system may decide whether adjustments to the measurement process are needed and if so, what kind adjustments are done. In this example, one possible adjustment is to reduce the number of reminders sent to the patient or reduce the degree of "intrusiveness" of the reminders. Because the blood glucose variance for breakfast time window is well under control, the system may even allow the patient to skip some measurements altogether. This naturally saves the resources required by the measurement process, e.g. lancets and measurement strips as well as effort required from the patient.

Figure 7:
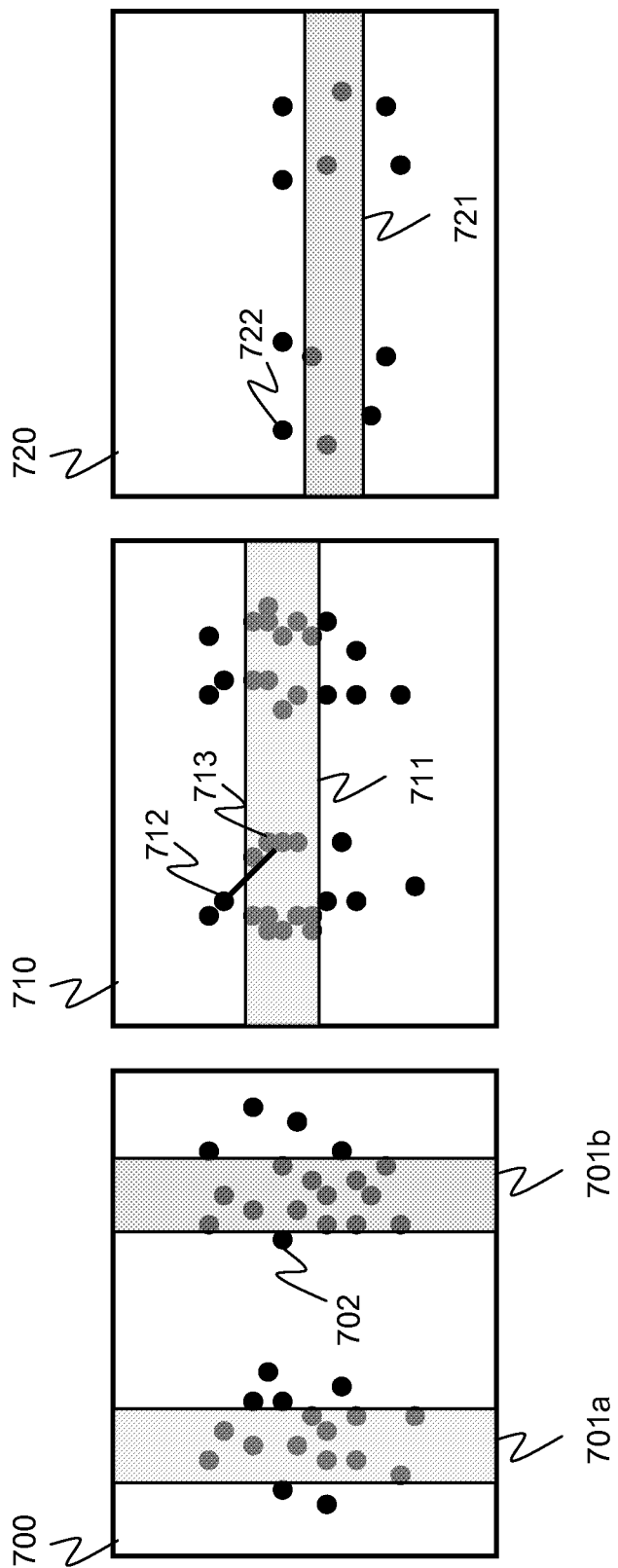
FIG. 7 shows different phases of the measurement process controllable using an embodiment of the method of the present invention.

FIG. 7 shows an exemplary method about drawing attention to the different aspects of controlling the blood glucose monitoring process according to an embodiment of the present invention. At first phase of the process, timing of the measurements is monitored. The diagram 700 shows individual measurement values 702 on the Y axis and the time of measurement event on the X axis. The shadowed areas 701a and 701b each represent a time window, e.g. breakfast and lunch. In the phase of diagram 700, the method concentrates on monitoring how punctual the measurement events are, i.e. how well they fit in the time window 701a and 701b. The less punctual the measurements are, the more the patient is guided towards punctual measurements by sending e.g. reminder messages to a mobile terminal or voicing an alarm by the blood glucose meter of the patient.

Once the measurements are punctual enough, e.g. at least 80% of the measurements occur when they are scheduled to occur, the measurement values are useful enough for the actual analysis. In the shown embodiment, there are two analysis phases. In the first analysis phase represented by diagram 710, the variance between the pair measurement values 712, 713 is analyzed. The goal is to guide the patient so that the variance stays within the allowed range 711. The allowed range may be adjusted separately for each patient. At this phase, if the measurements occur in a punctual manner, the measurement process does not necessarily remind the patient about each measurement separately, but e.g. provides feedback about the measurements, especially about the current level of the variance and about the direction of change of the variance.

Once the variance between pair measurement values is under control well enough, e.g. 80% of the values are within the allowed range 711, the patient's attention is guided towards adjusting the average blood glucose level to an optimum level. Diagram 720 shows measurement values 722 related to this phase of the monitoring process. If the timing and the variance of the measurement values stay within given limits 721, the patient is provided only feedback about e.g. the current average blood glucose level and its direction of change. However, if the e.g. timing and/or variance don't stay within the given limits or the direction of change of e.g. the variance or the average blood glucose level is adverse (i.e.

"getting worse"), the measurement control may switch e.g. back to previous phases 710 or 700 of the blood glucose monitoring process.

To a person skilled in the art, the foregoing exemplary embodiments illustrate the model presented in this application whereby it is possible to design different methods and arrangements, which in obvious ways to the expert, utilize the inventive idea presented in this application.

While the present invention has been described in accordance with preferred compositions and embodiments, it is to be understood that certain substitutions and alterations may be made thereto without departing from the spirit and scope of the following claims.

We claim:

1. A method for controlling a measurement process of blood glucose of a patient, comprising:
   selecting a repeatedly occurring event,
   a glucose meter obtaining a first measurement value of blood glucose, the first measurement value being associated with a first occurrence of the event,
   the glucose meter obtaining a second measurement value of blood glucose, the second measurement value being obtained after the first measurement value,
   the first and second measurement values forming a first pair of measurements associated with the first occurrence of the event,
   the glucose meter obtaining a second pair of measurement values associated with a second occurrence of the event,
   the second pair of measurement values occurring after the first pair of measurement values,
   the glucose meter sending the first and second pair of measurement values to a software program,
   the software program obtaining a first single difference value by determining a first difference between the first pair of measurement values,
   the software program obtaining a second single difference value by determining a second difference between the second pair of measurement values,
   the software program calculating trend data by comparing the first single difference value with the second single difference value, and
   software program controlling the measurement process using the trend data by sending a report message to a communication device of the patient.

2. The method according to claim 1, wherein the first single difference value is a combined average value calculated from difference data of multiple occurrences of the event.

3. The method according to claim 1, wherein the trend data comprises at least one difference data value and a direction of change of the difference data over time.

4. The method according to claim 1, wherein the measurement data comprises also information about absolute blood glucose level associated to the event or across a plurality of corresponding events.

5. The method according to claim 4, wherein the absolute blood glucose level information is used for controlling the measurement process when the trend data is within pre-determined limits.

6. The method according to claim 1, wherein the controlling the measurement process comprises altering a guidance status related to the event.

7. The method according to claim 1, wherein the controlling the measurement process comprises displaying needs for changes to a treatment regimen, and monitoring an effect of such changes.

8. The method according to claim 1, wherein the controlling the measurement process is at least partially accomplished using a processing power and data input/output of a blood glucose monitor.

9. The method according to claim 1, wherein the controlling the measurement process uses data storage and processing means of a remote server and/or other mobile devices.

10. The method according to claim 1, wherein the controlling the measurement process comprises sending a message to a mobile device of the patient.

11. The method according to claim 10, wherein the mobile device is a cellular phone.

12. The method according to claim 10, wherein the mobile device is a blood glucose meter.

13. The method according to claim 1, wherein the controlling the measurement process comprises displaying the trend data on a user interface of a web application.

* * * * *